(12) United States Patent
Werner et al.

(10) Patent No.: US 8,859,706 B2
(45) Date of Patent: Oct. 14, 2014

(54) BIOACTIVE HYDROGEL

(75) Inventors: Carsten Werner, Dresden (DE); Uwe Freudenberg, Dresden (DE); Dorit Meinhold, Dresden (DE); Marie-Francoise Gouzy, Allschwil (CH); Petra Welzel, Dresden (DE)

(73) Assignee: Zetascience GmbH, Dresden (DE)

( * ) Notice: Subject to any disclaimer, the term of this patent is extended or adjusted under 35 U.S.C. 154(b) by 543 days.

(21) Appl. No.: 13/131,295

(22) PCT Filed: Nov. 28, 2008

(86) PCT No.: PCT/EP2008/066484
§ 371 (c)(1),
(2), (4) Date: Nov. 22, 2011

(87) PCT Pub. No.: WO2010/060485
PCT Pub. Date: Jun. 3, 2010

(65) Prior Publication Data
US 2012/0058943 A1 Mar. 8, 2012

(51) Int. Cl.

| | |
|---|---|
| *A61L 33/08* | (2006.01) |
| *A61L 33/10* | (2006.01) |
| *A61L 33/12* | (2006.01) |
| *A61K 38/18* | (2006.01) |
| *A61K 47/42* | (2006.01) |
| *A61K 47/36* | (2006.01) |
| *C08B 37/10* | (2006.01) |
| *C08J 5/18* | (2006.01) |
| *C08J 3/075* | (2006.01) |
| *C08B 37/00* | (2006.01) |
| *C08L 5/10* | (2006.01) |
| *A61L 27/54* | (2006.01) |
| *A61L 27/52* | (2006.01) |
| *C08J 3/24* | (2006.01) |

(52) U.S. Cl.
CPC ............ *A61L 27/52* (2013.01); *A61L 2300/414* (2013.01); *C08J 5/18* (2013.01); *C08J 3/075* (2013.01); *C08B 37/0075* (2013.01); *C08B 37/0081* (2013.01); *C08L 5/10* (2013.01); *C08J 2371/02* (2013.01); *A61L 27/54* (2013.01); *A61L 2300/602* (2013.01); *C08J 2305/10* (2013.01); *C08J 3/246* (2013.01)
USPC ............. 527/312; 527/300; 514/7.6; 514/8.1; 514/9.1; 435/397; 523/112; 523/113

(58) Field of Classification Search
None
See application file for complete search history.

(56) References Cited

U.S. PATENT DOCUMENTS 6,306,922 B1  10/2001  Hubbell et al.
6,602,975 B2  8/2003   Hubbell et al.

FOREIGN PATENT DOCUMENTS

| WO | WO-2006/034467 | 3/2006 |
| WO | WO-2007/127198 | 11/2007 |
| WO | WO-2008/108736 | 9/2008 |

OTHER PUBLICATIONS

Salinas, C. et al "The enhancement of chondrogenic differentiation . . . " Biomaterials (2008) vol. 29, pp. 2370-2377.*
Braun, D. et al "Polymers from non-homopolymerizable monomers from free radical processes" Prog. Polym. Sci. (2005) vol. 31 pp. 239-276.*
Braun, D. et al "Free radical terpolymerization of trans-anethole . . . " J. Macromol. Sci. (2005) vol. 42, pp. 1127-1146 (abstract only).*
Harke Group product information for maleic anhydride accessed from the internet Jun. 9, 2014: http://www.harke.com/en/products/dicarbonic-acids-anhydrides-and-derivatives/maleic-acid-anhydride/maleic-anhydride-msa.html.*
Acros Organics Material Safety Data Sheet for maleic anhydride (2009).*
"PCT International Preliminary Report on Patentability", Jun. 9, 2011, 10 pages.
Nie, Ting et al., "Production of Heparin-Functionalized Hydrogels for the Development of Responsive and Controlled Growth Factor Delivery Systems", *Journal of Controlled Release*, vol. 122 2007, 287-296.
Seal, Brandon L. et al., "Physical Matrices Stabilized by Enzymatically Sensitive Covalent Crosslinks", *Acta Biomaterialia*, vol. 2, No. 3 2006, 241-251.
Yamaguchi, Nori et al., "Polysaccharide-Poly(ethylene glycol) Star Copolymer as a Scaffold for the Production of Bioactive Hydrogels", *Biomacromolecules*, vol. 6, No. 4 2005, 1921-1930.
Zhang, Le et al.., "Manipulation of Hydrogel Assembly and Growth Factor Delivery via the Use of Peptide-Polysaccharide Interations", *Journal of Controlled Release*, vol. 114 2006, 130-142.
Zhang, Xianzhong et al., "Preparation and Characterization of 99M Tc(CO)3-BPy-RGD Complex as alphavbeta3 Integrin Receptor-Targeted Imaging Agent", *Applied Radiation and Isotopes*. vol. 65, No. 1 2007, 70-78.
"RGD Peptides Molecular Glue? A Cell Adhesion Motiff", *Peptides International* Sep. 25, 2006, 2 pgs.

* cited by examiner

*Primary Examiner* — Leigh Maier
(74) *Attorney, Agent, or Firm* — Servilla Whitney LLC

(57) ABSTRACT

The invention relates to a bioactive hydrogel as a hybrid material of heparin and star-branched polyethylene glycol with functionalized end groups, wherein the heparin is bound directly by reaction of the carboxyl groups activated with 1-ethyl-3-(3-dimethylaminopropyl) carbodiimides/N-hydroxysulfosuccinimide (EDC/s-NHS) with the terminal amino groups of the polyethylene glycol covalently by amide bonds.

21 Claims, 1 Drawing Sheet

SEQUENCE LISTING

```
<160> NUMBER OF SEQ ID NOS: 3

<210> SEQ ID NO 1
<211> LENGTH: 5
<212> TYPE: PRT
<213> ORGANISM: Artificial Sequence
<220> FEATURE:
<223> OTHER INFORMATION: Adhesion peptide
<220> FEATURE:
<221> NAME/KEY: MISC_FEATURE
<222> LOCATION: (1)..(5)
<223> OTHER INFORMATION: cyclized peptide
<220> FEATURE:
<221> NAME/KEY: MISC_FEATURE
<222> LOCATION: (4)..(4)
<223> OTHER INFORMATION: D-amino acid

<400> SEQUENCE: 1

Arg Gly Asp Tyr Lys
1               5

<210> SEQ ID NO 2
<211> LENGTH: 8
<212> TYPE: PRT
<213> ORGANISM: Artificial Sequence
<220> FEATURE:
<223> OTHER INFORMATION: enzymatically cleavable peptide

<400> SEQUENCE: 2

Gly Pro Gln Gly Ile Ala Gly Gln
1               5

<210> SEQ ID NO 3
<211> LENGTH: 8
<212> TYPE: PRT
<213> ORGANISM: Artificial Sequence
<220> FEATURE:
<223> OTHER INFORMATION: enzymatically cleavable peptide sequence

<400> SEQUENCE: 3

Gly Pro Gln Gly Ile Trp Gly Gln
1               5
```

BIOACTIVE HYDROGEL

CROSS-REFERENCE TO RELATED APPLICATIONS

This application is a National Phase entry of International Application No. PCT/EP2008/066484, filed Nov. 28, 2008.

REFERENCE TO SEQUENCE LISTING

The material contained in the text file identified as "SFH0001-00US Sequence Listing_ST25.txt" (created May 25, 2011; 1,018 bytes) is hereby incorporated by reference.

BACKGROUND

The invention relates to a bioactive hydrogel, which can be used as biomaterial for replacing biological tissue, as an implant material or in the broadest sense in medicinal products.

"Biomaterial" means, in the sense of the invention, materials that are brought into contact with a biological organism in diagnostic or therapeutic applications. These materials must meet special requirements with respect to biocompatibility. "Biocompatibility" means the absence of clinically significant reactions of the organism to the use of materials, medicinal products or medical systems.

Bioactive hydrogels of this kind are used particularly advantageously as implant or tissue-replacement materials.

Various approaches for production of bioactive hydrogels are known in the prior art. Various implant or tissue-replacement materials have been investigated for use in regenerative therapies, for example for supporting the regeneration of blood vessels and nerve tracts or as skin replacement materials. For this, framework or carrier materials, so-called scaffolds, have been developed based on biological or synthetic main components, which after transplantation are intended temporarily to perform important functions of the natural extracellular matrix ECM. Cells in natural tissues exist within this ECM. The ECM is a complex, supramolecular network of various structural proteins, mainly collagen, proteoglycans, glycoproteins and elastin, whose structural organization and functional composition are essential for maintaining normal tissue architecture and for tissue-specific functions.

According to the current level of science, so-called scaffolds, which primarily perform a carrying and supporting function for the cells of importance for the regeneration processes and provide protection against mechanical stresses, are used for the aforementioned regenerative processes. For example, the use of highly hydrated materials, so-called hydrogels with synthetic or biological main components, which are degradable in the body over quite long periods without cell-damaging effects, is known from U.S. Pat. Nos. 6,306,922 A and 6,602,975.

So as to be able to support even complex multicellular processes, mixtures of components of the natural ECM or also materials for reversible binding and release of therapeutically relevant signal molecules have also been developed. For the last-mentioned functions, combinations of synthetic and polysaccharide-based components of the natural ECM have also been developed, which exploit the special affinity of these molecules for important signal molecules, for example growth factors.

A disadvantage of the materials known in the prior art is that the complex therapeutic problems of the known hydrogels are not solved sufficiently effectively in all respects. Moreover, most of the materials hitherto described are restricted to a narrow range in their physical properties, in particular in their mechanical properties, relating to stiffness and swelling, due to the limitations of crosslinking chemistry or the exclusive use of natural substances.

SUMMARY

The problem to be solved by the invention is to make available a highly hydrated, gel-like material with required gradations of physical and biochemical properties, and a method of production of said material.

The material must be degradable in the long term in the body without toxic breakdown products and must be biocompatible. Furthermore, the material should offer the possibility of performing all important functions of the natural extracellular matrix modularly, i.e. largely independently of one another.

The detailed problems flowing from this are:
to improve the structural, supporting and protective function for ingrowing cells specifically, depending on the area of application,
to make control of cell adhesion possible,
to permit the reversible binding and release of therapeutically relevant signal molecules and
to create the possibility of restructuring by ingrowing cells as required.

The aforementioned problem is solved with a bioactive hydrogel as hybrid material of heparin and star-branched polyethylene glycol with functionalized end groups, wherein the heparin is bound directly by 1-ethyl-3-(3-dimethylaminopropyl) carbodiimides/N-hydroxysulfosuccinimide (EDC/s-NHS) activated carboxyl groups of heparin to the terminal amino groups of the polyethylene glycol covalently by amide bonds.

Alternatively the problem is solved with a bioactive hydrogel as a hybrid material of heparin and star-branched polyethylene glycol with functionalized end groups, wherein the heparin is bound covalently to the polyethylene glycol via short enzyme-cleavable peptide sequences as crosslinking molecule.

There are two possible routes:

The first route goes via the functionalization of the PEG, wherein the functionalization of the polyethylene glycol with enzyme-cleavable peptide sequences takes place by reaction of the carboxyl group activated with 1-ethyl-3-(3-dimethylaminopropyl) carbodiimides/N-hydroxysulfosuccinimide (EDC/s-NHS) on the C-terminus of the peptide with the amino groups of the polyethylene glycol, and then gel formation proper takes place by reaction of the amino group on the N-terminus of the peptide bound to the PEG with the carboxyl groups of heparin activated with 1-ethyl-3-(3-dimethylaminopropyl) carbodiimides/N-hydroxysulfosuccinimide (EDC/s-NHS).

The second route goes via the functionalization of heparin, wherein the functionalization of heparin with enzyme-cleavable peptide sequences takes place by reaction of the carboxyl groups of heparin activated with 1-ethyl-3-(3-dimethylaminopropyl) carbodiimides/N-hydroxysulfosuccinimide (EDC/s-NHS) with the amino group on the N-terminus of the peptide, and then gel formation proper takes place by reaction of heparin functionalized with the peptides, by reaction of the carboxyl group on the C-terminus of the peptide activated with 1-ethyl-3-(3-dimethylaminopropyl) carbodiimides/N-hydroxysulfosuccinimide (EDC/s-NHS), with the amino groups of the PEG.

Subsidiary embodiments of the invention comprise providing a film of the hydrogels according to the invention, which is obtainable by dropwise application of a defined amount of liquid gel materials on carrier surfaces which have been rendered hydrophobic, in particular cover glass or silicon wafer, gel formation after covering the carrier surfaces with glass carrier or silicon wafer which have been rendered hydrophobic, transferring the carrier surfaces to a washing solution and removing the films after swelling of the hydrogels.

The films that can be produced have in preferred embodiments a thickness of 80 to 2000 µm, and even films with thicknesses of several millimeters can be produced from this material and by the stated method.

The washing solution used is preferably PBS.

A further application arising from the invention is that it is possible to produce hollow cylinder-shaped, tubular formed pieces from hydrogels according to the invention with a length of up to 7 cm and an inside diameter of 0.1 to 0.8 mm.

The tubular structures are obtained for example by injecting still-liquid hydrogel into a capillary-shaped tube of reconstituted cellulose and then introducing a retainer into the tube, after which the bioactive hydrogel is formed and the retainer is then removed.

A further application of the invention comprises a cell culture support with a hydrogel according to the invention, wherein the hydrogel is coupled covalently by means of thin layers of reactive polymers of alternating MSA copolymers, wherein gel formation is carried out in the presence of polymer-coated inorganic carriers containing anhydride groups and the hydrogels are bound via the amino groups of the star-shaped polyethylene glycol to the inorganic carriers.

The method of production of bioactive hydrogel according to the invention is characterized in that a) the components heparin,
1-ethyl-3-(3-dimethylaminopropyl) carbodiimides EDC, sulfo-N-hydroxysulfosuccinimide s-NHS and star-shaped polyethylene glycol star-PEG are dissolved separately, and then b) EDC and s-NHS are mixed together as activation reagents for the carboxyl groups of the heparin, wherein c) the heparin is activated by adding EDC and s-NHS and then d) star-PEG is added and the mixture is homogenized and e) gel formation then takes place, wherein f) following gel formation, the finished formed gel is washed.

An advantageous embodiment of the method comprises a) dissolving the components heparin,
1-ethyl-3-(3-dimethylaminopropyl) carbodiimides EDC, sulfo-N-hydroxysulfosuccinimide s-NHS and star-shaped polyethylene glycol star-PEG separately in deionized water at 4° C., and then b) mixing EDC and s-NHS as activation reagents for the carboxyl groups of heparin in the ratio 2 to 1, wherein c) activation of heparin after adding EDC and s-NHS takes place for 15 min at 4° C. and then d) star-PEG is added and the mixture is homogenized at 8° C. for 15 min and e) gel formation takes place for a period of 1 to 14 h at room temperature, wherein f) then the finished formed gel is washed with phosphate-buffered sodium chloride solution or alternately in acid or basic salt solutions and in phosphate-buffered sodium chloride solution.

Preferably the ratio of EDC and s-NHS relative to the amino groups of star-PEG is 1.75 to 1, and the ratio of star-shaped polyethylene glycol to heparin is from 1 to 1 to 6 to 1.

The method of production of the hydrogels is advantageously supplemented in that, after step f), the hydrogel is modified with an adhesion protein, wherein the washed hydrogel is activated with a solution of EDC/s-NHS in 1/15 M phosphate buffer with pH=5 for 30 min at 4° C., after which the solution is replaced with a solution of 100 mM borate buffer of pH=8 containing 0.2 mg/ml RGD peptide as adhesion protein and is immobilized for 2 h at room temperature, after which the modified hydrogel is rinsed with PBS again.

As RGD peptide, advantageously cycloRGDyK (SEQ ID NO:1) is used as adhesion protein.

In an advantageous further development of the method, the hydrogel is loaded with the growth factors basic fibroblast growth factor b-FGF and vascular endothelial growth factor VEGF, wherein the hydrogels are incubated with a solution of b-FGF or VEGF with a concentration of 1-5 µg/ml in PBS for 4 to 24 h at room temperature and are then washed in PBS.

DETAILED DESCRIPTION

Figure 1:
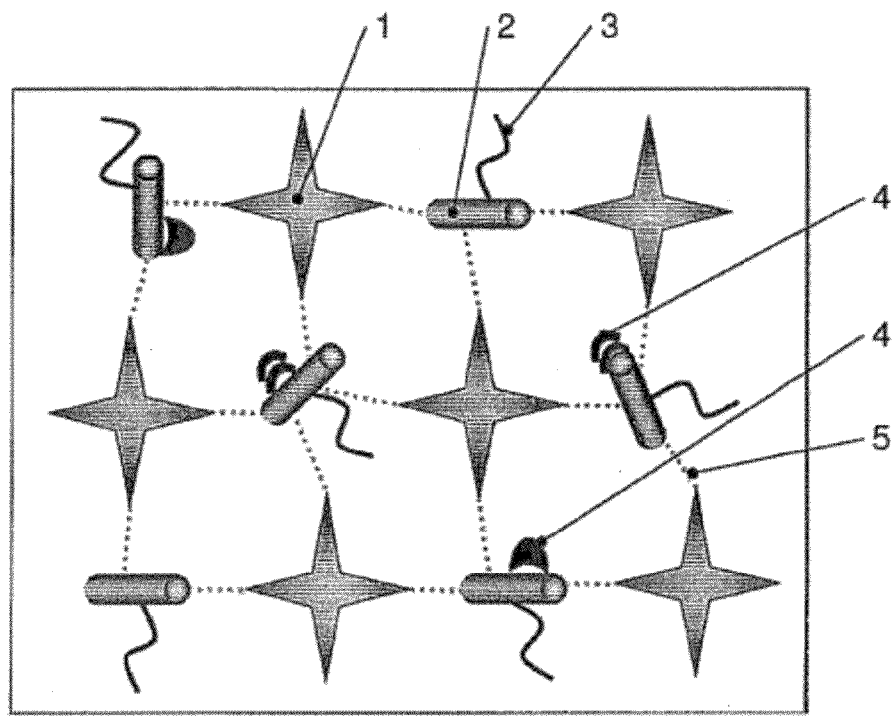
FIG. 1 is a schematic representation of the synthetic hydrogel of heparin and amino end-functionalized, star-branched polyethylene glycol.

The idea of the invention is that the desired properties of the hydrogels are realized by the synthesis of a hybrid material from a biologically active component—the natural ECM component heparin—and a synthetic, star-branched polyethylene glycol with functionalized end groups (star-PEG). These two constituents form the framework structure, the scaffold proper.

Depending on the application, these two main components—carboxyl groups of heparin activated directly by 1-ethyl-3-(3-dimethylaminopropyl) carbodiimides/N-hydroxysulfosuccinimide (EDC/s-NHS) and the terminal amino groups of the star-PEG —are bound covalently by amide bonds.

Alternatively the analogous coupling chemistry is used, in order to bind short enzyme-cleavable peptide sequences as crosslinking molecule between star-PEG and heparin. The advantage of this is the synthesis of a network of star-PEG and heparin joined together covalently, which can be degraded locally by the enzyme activity of individual cells by cleavage of the peptide bridges. As a result, a partial restructuring and replacement of the synthetic matrix with material secreted by the cells is possible, moreover it is possible for the cells to migrate into the material and unite, to form therapeutically important structures, for example capillary-shaped blood vessels. Regardless of the type of crosslinking—either directly between heparin and star-PEG or via the cleavable peptide sequences—the physical properties of the scaffold can be varied over a wide range. The cell adhesion of the materials is controlled by the targeted modification of heparin with short peptide sequences, for example by integrin-binding arginine-glycine-aspartic acid (RGD) sequences.

The biofunctional component, heparin, is used, as well as for control of cell adhesion, also for controlled binding and release of therapeutically relevant signal molecules, for example growth factors. The generally known high affinity of the strongly negatively charged heparin for a large number of growth factors, for example bFGF and VEGF, makes possible the reversible and nature-identical electrostatic binding and release of these signal molecules, which are important for a large number of regenerative processes. Loading and release can moreover be influenced to some extent by the network structure, characterized by the mesh size and degree of crosslinking of the hydrogel materials. A particular advantage is that all components are moreover completely biodegradable and that PEG and heparin are permitted for human therapeutic use for example by the American medicinal product authorization authority, the Food and Drug Administration (FDA).

The advantages according to one or more embodiments of the invention can be summarized as follows:

As a key property and therefore a decisive advantage over the currently available materials, the hydrogels according to embodiments of the invention can overcome the drawbacks of the prior art, i.e. lack of important functions of the ECM.

The scaffold of the hydrogels according to embodiments of the invention, with widely varying physical properties, for example stiffness and hydration, forms the structural, supporting and protective function for ingrowing cells. Owing to the wide range of stiffness, the materials are transplantable either in minimally invasive conditions by injection or as prefabricated parts with form and function.

The physical properties are varied as required via the quality and quantity of the coupling points within the network of the hydrogels. The quality of coupling is determined conceptually by means of the coupling mechanisms used and/or via the modified components, whereas the quantity of coupling is determined by the relative proportions of the components and the activation parameters.

The well-known resistance of PEG materials to nonspecific protein adsorption reduces unwanted, uncontrolled interactions with biomolecules, whereas interaction with the therapeutically active cells and microorganisms can be controlled and regulated by targeted modification with cell adhesion proteins (RGD peptides). The adequate presentation of heparin in the network allows reversible binding and release of therapeutically relevant signal molecules, and the possibility of restructuring as required by ingrowing cells is realized by crosslinking by enzymatically cleavable peptide bridges.

Another substantial advantage is the modular character of the hydrogels. In addition to wide variation of physical properties by means of the degree of crosslinking, biofunctionalization is also possible in modular fashion, for example control of cell adhesion by means of RGD peptides, direct crosslinking or crosslinking with enzyme-cleavable peptides and loading with growth factors can be varied independently of one another and over a wide range.

These properties mean that the bioactive hydrogels can be used long-term, for periods from several weeks to months.

Depending on the particular application, by varying the relative proportions of the components and by varying the process parameters, different physical properties can be produced intentionally for different types of tissues, for adequately cultivating the endogenous cells that are to become attached or are to migrate into the structure. This is particularly apparent if for example we consider the requirements for nerve or muscle cells. For this reason it is advantageous if implant materials have properties that can be varied over a wide range.

In contrast to the prior art, the combination of the possibility of restructuring the molecular structures by ingrowing cells and the natural binding of signal molecules, in particular growth factors, to the bioactive component heparin is a decisive development step. In the hydrogels according to the invention, this advantage is achieved in that the possibility for restructuring according to requirements by inward-migrating cells is provided similarly to the natural mechanisms in the ECM, since the signal molecules are bound reversibly.

Especially preferred areas of application of the hydrogels according to the invention are the use as implant materials in regenerative therapies, for example to support the regeneration of blood vessels by means of injectable gels, for nerve tracts both of the central and of the peripheral nervous system as tubular structures and as temporary corneal substitute when using films.

Further details, features and advantages of the invention will become clear from the following description of examples, referring to the accompanying drawings.

FIG. 1 is a schematic representation of the synthetic hydrogel of heparin and amino end-functionalized, star-branched polyethylene glycol.

The star-branched, amino end-functionalized polyethylene glycol 1 is bound by enzymatically cleavable peptide sequences 5 in each case to heparin molecules 2 to form a network. The heparin molecules 2 have in addition RGD peptides 3, i.e. integrin-binding arginine-glycine-aspartic acid (RGD) sequences. Various signal molecules 4 attached to the heparin 2 are also shown schematically.

The basic method of production of bioactive hydrogel can be described as follows:

The components heparin, EDC, s-NHS and star-PEG are dissolved separately in deionized water on ice at 4° C. The ratio of the activation reagents for the carboxyl groups of heparin is EDC to s-NHS equal to 2 to 1. After dissolution, the EDC/s-NHS is added to the heparin and the carboxyl groups of heparin are activated for 15 min at 4° C. Then the star-PEG is added and the mixture is homogenized at 8° C. for 15 min (at 900 rev/min, Thermomixer Comfort, Eppendorf, Hamburg, Germany). Next, further gel formation takes place for a period of 1 to 14 h at room temperature, followed by multiple (at least 5 times, for a period of 1 h) washing steps in PBS—alternatively the prepared gels are rinsed alternately in acid or basic salt solutions and in PBS.

Alternatively, star-PEG functionalized with enzyme-cleavable peptides or heparin is used for crosslinking; the technical procedure is similar to the method described above.

The basic procedure described above can now be modified in each case under specific boundary conditions, in order to produce particular required properties of the hydrogels.

(A) Hydrogels are synthesized according to the basic method by direct reaction of EDC (Sigma-Aldrich, Munich, Germany)/s-NHS (Sigma-Aldrich, Munich, Germany) activated carboxyl groups of heparin (MW 14 000, Calbiochem (Merck), Darmstadt, Germany) with the amino groups of star-PEG (MW 10 000, Polymer Source, Inc., Dorval, Canada). Relative to the amino groups of the star-PEG, EDC/s-NHS is used in the ratio EDC 1.75 to 1 amino groups.

The ratio of heparin to star-PEG determines the degree of crosslinking and therefore the physical properties of the resultant gel materials. Molar ratios of star-PEG to heparin from 1 to 1 to 6 to 1 are used for this. The designation of the gels in FIG. 2 as type 1 to type 6 is derived from these molar ratios.

Figure 2:
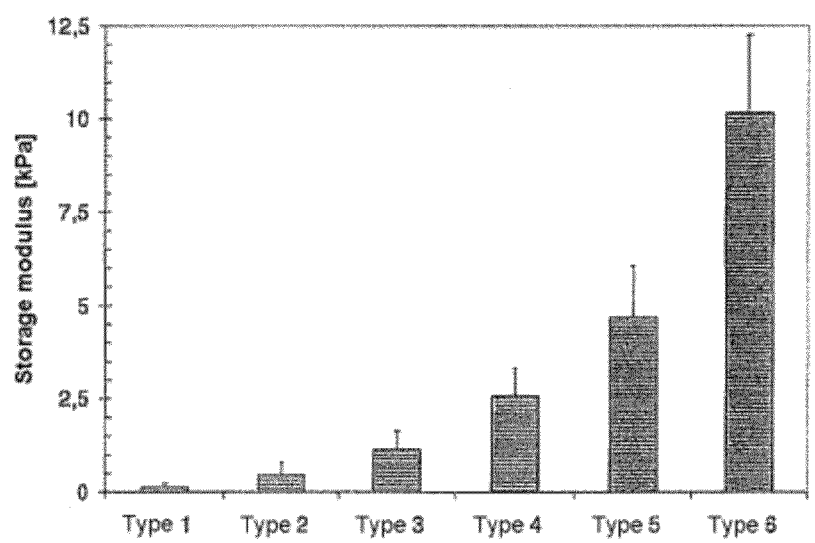
FIG. 2 is a graph showing the storage modulus as a function of the type of the individual embodiments of hydrogels.

The physical properties resulting from the variation of the ratios are evident from the presentation in FIG. 2.

(B) According to another embodiment of the invention, hydrogels are produced according to the basic method, which differ from the embodiment in (A) by the heparin used. Instead of heparin 14 000 MW, a heparin with shorter chain length of 4000 MW (Sigma-Aldrich, Munich, Germany) is used.

(C) In this embodiment of the invention, hydrogels are produced according to the basic method, which again differ from (A) by the heparin used. Instead of unmodified heparin 14 000 MW, a heparin modified with enzymatically cleavable peptide sequences is used. The enzymatically cleavable peptide sequences are characterized by the single-letter code: GPQG↓IAGQ (SEQ ID NO:2) or GPQG↓IWGQ (SEQ ID NO:3) and are produced by solid-phase peptide synthesis.

(D) In this embodiment, the hydrogel is produced according to the basic method and once again differs from the embodiment in (A) by the heparin used. Instead of unmodified heparin 14 000 MW, a heparin modified with adhesion protein (sequence: cycloRGDyK, Peptides International, Louisville, Ky., USA) is used.

(E) The hydrogel is once again produced according to the basic method, wherein the embodiments (A to D) differ by the star-PEG used. In this case, instead of star-PEG 10 000 MW, a star-PEG of molecular weight 19 000 MW (Polymer Source, Inc., Dorval, Canada) is used.

In a variant of this embodiment, instead of unmodified PEG 10 000 MW/19 000 MW, a star-PEG modified with enzymatically cleavable peptide sequences is used. The enzymatically cleavable peptide sequences are characterized by the single-letter code: GPQG↓IAGQ (SEQ ID NO: 2) or GPQG↓IWGQ (SEQ ID NO:3) and are produced by solid-phase peptide synthesis.

(F) According to another embodiment, the hydrogels are produced as described in (A, B, C and E), and after the washing step are then modified with adhesion proteins (generally RGD peptide, e.g. cycloRGDyK, SEQ ID NO:1). For this, the washed gel materials are activated with a solution of EDC/s-NHS in 1/15 M phosphate buffer (pH=5) for 30 min at 4° C. Next, the solution is replaced with a solution of 100 mM borate buffer (pH=8) containing 0.2 mg/ml (cycloRGDyK, SEQ ID NO:1) and is immobilized for 2 h at room temperature. As the final step, the materials are again rinsed several times with PBS.

(G) All hydrogels of the embodiments (A to F) are then, according to another advantageous embodiment, loaded with growth factors (b-FGF or VEGF). For this, the gel materials, dissolved with b-FGF or VEGF (1-5 μg/ml), were incubated in PBS for 4 to 24 h at room temperature. Then the materials were washed in PBS.

(H) Because of the lower degree of crosslinking, the hydrogels of types 1, 2, 3 and 4 can be injected with a commercially available syringe of gauge size 27.

(I) On account of their stiffness, the hydrogels of types 5 and 6 according to examples (A to G) are also suitable for the production of formed pieces. Tubular structures up to 7 cm in length and with an inside diameter from 0.3 to 0.8 mm can be produced.

(J) In another embodiment, tubular structures are produced in the form of a hybrid system of a tube and gel materials of types 1 to 6 according to the examples (A to G). For this, a capillary-shaped tube (for example made of reconstituted cellulose) with inside diameter in the range from 0.3 to 0.8 mm is filled by injection with the already mixed, still liquid gel materials and then a retainer, for example a glass rod with an outside diameter in the range from 0.2 to 0.5 mm, is inserted. After gel formation, the hybrid systems are swollen and the retainer inside is removed. This results in hybrid tubes of a tubular carrier material, with the hydrogel inside. The advantage of this hybrid system is the possibility of using all gel types inside, even gel types with low storage modulus and/or low stiffness.

(K) Another alternative use of the hydrogels is for films with a thickness from about 80 to 2000 μm. Diameters from 15 to 25 mm are produced from the gels of types 5 or 6 of the examples (A to G) by dropwise application of a defined amount of liquid gel materials onto cover glasses or silicon wafers which have been rendered hydrophobic, which are then covered again with glass carriers/silicon wafers which have been rendered hydrophobic. After gel formation, the glass carriers are transferred to PBS and can thus easily be removed by swelling.

(L) The gel materials of types 1 to 6 of examples (A to G) were covalently coupled via thin layers of reactive polymers (alternating MSA copolymers) for 2D cell culture supports. For this, gel formation is carried out in the presence of polymer-coated inorganic carriers containing anhydride groups and therefore the gel materials are bound via the amino groups of the star-PEG to the inorganic carriers.

The advantages and the efficacy of the disclosed embodiments were verified experimentally.

The materials obtained according to the various embodiments of the invention permit, owing to the nature of the chemical bonds, gradation of the physical properties over a wide range. The storage modulus, as a key parameter for describing the stiffness of the materials and the degree of swelling of the materials can, depending on the degree of crosslinking, be varied over a wide range by varying the individual parameters. FIG. 2 shows the storage modulus as a function of the type of the individual embodiments of hydrogels.

The storage modulus was determined with oscillating measurements on swollen gels in PBS on a rotating rheometer of the company ARES (ARES LN2, TA Instruments, Eschborn, Germany). The geometry used was a plate/plate arrangement (plate diameter 25 mm, the gap between them was in the range from 1.2 to 1.5 mm). The measurements were carried out at 25° C. in a frequency range of 10+2-10-1 rad×s-1. The amplitude of deformation was set at 3%. The storage modulus was measured as a function of the shear frequency. The mean values of the storage modulus in the frequency range between 100-101 rad×s-1 were determined from at least 3 independent measurements.

LIST OF REFERENCE SYMBOLS

1 star-shaped polyethylene glycol, (PEG), star-PEG
2 heparin
3 integrin-binding arginine-glycine-aspartic acid (RGD) sequences
4 signal molecules
5 enzymatically cleavable peptide sequences Abbreviations in the Description ECM extracellular matrix
EDC 1-ethyl-3-(3-dimethylaminopropyl) carbodiimides
s-NHS sulfo-N-hydroxysulfosuccinimide
bFGF basic fibroblast growth factor
VEGF vascular endothelial growth factor
PBS phosphate-buffered sodium chloride solution
PEG polyethylene glycol MSA maleic anhydride

The invention claimed is:

1. A bioactive hydrogel comprising a hybrid material of heparin and star-branched polyethylene glycol with functionalized end groups, wherein the heparin is bound covalently to the polyethylene glycol via enzyme-cleavable peptide sequences as cros slinking molecules.

2. The bioactive hydrogel according to claim 1, wherein the functionalization of the polyethylene glycol with enzyme-cleavable peptide sequences takes place by reaction of the carboxyl group on the C-terminus of the peptide, activated with 1-ethyl-3-(3-dimethylaminopropyl) carbodiimides/N-hydroxysulfosuccinimide (EDC/s-NHS), with the amino groups of the polyethylene glycol and then the gel is formed by reaction of the amino group on the N-terminus of the peptide bound to the PEG with the carboxyl groups of heparin activated with 1-ethyl-3-(3-dimethylaminopropyl) carbodiimides/N-hydroxysulfosuccinimide (EDC/s-NHS).

3. The bioactive hydrogel according to claim 1, wherein the functionalization of heparin with enzyme-cleavable peptide sequences takes place by reaction of the carboxyl groups of heparin activated with 1-ethyl-3-(3-dimethylaminopropyl) carbodiimides/N-hydroxysulfosuccinimide (EDC/s-NHS) with the amino group on the N-terminus of the peptide and then the gel is formed by reaction of heparin functionalized with the peptides, by reacting the carboxyl group on the C-terminus of the peptide activated with 1-ethyl-3-(3-dimethylaminopropyl) carbodiimides/N-hydroxysulfosuccinimide (EDC/s-NHS) with the amino groups of the PEG.

4. The bioactive hydrogel according to claim 1, further comprising an adhesion protein.

5. The bioactive hydrogel according to claim 1, wherein therapeutically relevant signal molecules are coupled reversibly, electrostatically to the heparin.

6. The bioactive hydrogel according to claim 5, wherein growth factors are coupled reversibly, electrostatically to the heparin.

7. The bioactive hydrogel according to claim 6, wherein bFGF or VEGF is coupled reversibly, electrostatically to the heparin, as growth factor.

8. The bioactive hydrogel according to claim 1, wherein the heparin has a chain length of 4000 to 14 000 MW.

9. The bioactive hydrogel according to claim 1, wherein the star-PEG has a molecular weight of 10 000 to 19 000 MW.

10. The bioactive hydrogel according to claim 1, wherein the enzyme-cleavable peptide sequence is GPQG↓IAGQ or GPQG↓IWGQ.

11. The bioactive hydrogel according to claim 1, wherein the heparin is modified with an adhesion protein of sequence cycloRGDyK.

12. A film comprising the hydrogel according to claim 1, wherein the film is prepared by
- dropwise application of a defined amount of liquid components for forming the hydrogel on carrier surfaces which have been rendered hydrophobic,
- gel formation after covering the carrier surfaces with cover surfaces which have been rendered hydrophobic,
- transfer of the carrier surfaces to a washing solution and
- removal of the film after swelling of the hydrogels on the carrier surfaces.

13. A cell culture support comprising the hydrogel according to claim 1, wherein the hydrogel is coupled covalently via thin layers of reactive polymers of alternating maleic anhydride (MSA) copolymers, gel formation being carried out in the presence of polymer-coated inorganic carriers containing anhydride groups and the hydrogels being bound via the amino groups of star-PEG to the inorganic carrier.

14. A method of production of the bioactive hydrogel according to claim 1, wherein
- a) the components heparin,
  1-ethyl-3-(3-dimethylaminopropyl) carbodiimides EDC, sulfo-N-hydroxysulfosuccinimide s-NHS and star-shaped polyethylene glycol star-PEG functionalized with the enzyme-cleavable peptide sequence are dissolved separately, after which
- b) EDC and s-NHS are mixed together as activation reagents for the carboxyl groups of heparin, and
- c) the heparin is activated by adding EDC and s-NHS and then
- d) star-PEG functionalized with the enzyme-cleavable peptide sequence is added and the mixture is homogenized and
- e) gel formation then takes place, and
- f) after that, the finished formed gel is washed.

15. The method according to claim 14, wherein
- a) heparin,
  1-ethyl-3-(3-dimethylaminopropyl) carbodiimides EDC, sulfo-N-hydroxysulfosuccinimide s-NHS and star-shaped polyethylene glycol star-PEG functionalized with the enzyme-cleavable peptide sequence are dissolved separately in deionized water at 4° C., after which
- b) EDC and s-NHS are mixed together as activation reagents for the carboxyl groups of heparin in the ratio of two to one, and
- c) activation of heparin takes place after adding EDC and s-NHS for 15 min at 4° C. and then
- d) star-PEG is added and the mixture is homogenized at 8° C. for 15 min and
- e) gel formation takes place for a period of 1 to 14 h at room temperature, and
- f) then the finished formed gel is washed with phosphate-buffered sodium chloride solution or alternately in acid or basic salt solutions and in phosphate-buffered sodium chloride solution.

16. The method according to claim 14, wherein the ratio of EDC and s-NHS relative to the amino groups of star-PEG is 1.75 to 1, and the ratio of star-PEG to heparin is from 1 to 1 to 6 to 1.

17. The method according to claim 14, wherein the hydrogel is modified after step f) with the adhesion protein cycloRGDyK, and the washed hydrogels are activated with a solution of EDC/s-NHS in 1/15 M phosphate buffer at pH=5 for 30 min at 4° C., after which the solution is replaced with a solution of 100 mM borate buffer of pH=8 containing 0.2 mg/ml cycloRGDyK and is immobilized for 2 h at room temperature, after which the modified hydrogel is rinsed with PBS again.

18. The method according to claim 14, wherein the hydrogel is loaded with growth factors b-FGF or VEGF, wherein the hydrogels are incubated with a solution of b-FGF or VEGF with a concentration of 1-5 µg/ml in PBS for 4 to 24 h at room temperature and are then washed in PBS.

19. The bioactive hydrogel according to claim 1 which is in the form of a film or a tubular structure comprising a capillary-shaped tube with the bioactive hydrogel according to claim 1 inside the tubular structure.

20. A 2-dimensional cell culture support comprising the bioactive hydrogel according to claim 1 covalently coupled via a layer of alternating maleic anhydride (MSA) copolymers to an inorganic carrier containing anhydride groups.

21. A method of production of the bioactive hydrogel according to claim 1, wherein
- a) the components heparin functionalized with the enzyme cleavable peptide sequence,
  1-ethyl-3-(3-dimethylaminopropyl) carbodiimides EDC, sulfo-N-hydroxysulfosuccinimide s-NHS and star-shaped polyethylene glycol star-PEG are dissolved separately, after which
- b) EDC and s-NHS are mixed together as activation reagents for the carboxyl groups of the enzyme cleavable peptide sequence, and
- c) the enzyme cleavable peptide sequence is activated by adding EDC and s-NHS and then
- d) star-PEG is added and the mixture is homogenized and
- e) gel formation then takes place, and
- f) after that, the finished formed gel is washed.

* * * * *